United States Patent

Kutchko

[11] Patent Number: 6,039,938
[45] Date of Patent: Mar. 21, 2000

[54] BUOYANT DEODORIZER BAR

[76] Inventor: Joseph Kutchko, Rte. 910, R.D. 3, Allison Park, Pa. 15101-9803

[21] Appl. No.: 08/912,745

[22] Filed: Aug. 18, 1997

[51] Int. Cl.$^7$ ........................................................ A61L 9/00
[52] U.S. Cl. ........................................... 424/76.1; 424/401
[58] Field of Search ..................................... 424/76.1, 401

[56] References Cited

U.S. PATENT DOCUMENTS

| | | | |
|---|---|---|---|
| 3,668,717 | 6/1972 | Curran | 4/231 |
| 4,117,110 | 9/1978 | Hautmann | 424/76 |
| 4,833,181 | 5/1989 | Narukawa et al. | 524/13 |
| 5,642,871 | 7/1997 | Repert et al. | 248/686 |

OTHER PUBLICATIONS

Whether They Cover or Kill, Air Fresheners Smell Like Big Business, Brandweek, p. 34, Feb. 22, 1993.

*Primary Examiner*—Jose' G. Dees
*Assistant Examiner*—Kathryne E. Shelborne
*Attorney, Agent, or Firm*—Susan E. Nagel, Esq.

[57] ABSTRACT

The present invention provides a permanent buoyant hollow metallic device for removal of odors on hands.

3 Claims, 2 Drawing Sheets

BUOYANT DEODORIZER BAR

BACKGROUND

1) Field of the Invention

The present invention relates to permanent, hollow, buoyant, metallic deodorizer bars. The disclosure provides an object which floats in water and removes odor on hands upon rubbing it and flushing with liquid.

2) Description of the Related Art

The design for a metallic device to remove odors and a deodorizer bar have been disclosed in U.S. Pat. No. Des. 367,526 and U.S. Pat. No. Des. 339,857. The present invention discloses an improved metallic device which is able to float, and thus be readily found in a body of water. The device is advantageous over soap bars which exist in the prior art, as it does not dissolve or change consistency over time.

SUMMARY OF INVENTION

The present invention provides a permanent, hollow, buoyant device for removal of odors on hands. The removal of odor from hands may be accomplished by the utilization of soap, sprays, water, and perfumes. Odors may also be removed via the process of absorption using a metallic substance. The present invention is a permanent, hollow, buoyant, metallic bar which upon rubbing removes odor as odor molecules bond to the metallic bar instead of hands and are then washed away by liquid. The present invention is an improvement over prior art as the present invention is able to float and thus be readily found in a body of water. The device is advantageous over soap bars which exist in the prior art, as it does not dissolve or change consistency over time.

DESCRIPTION OF PREFERRED EMBODIMENT

Figure 1:
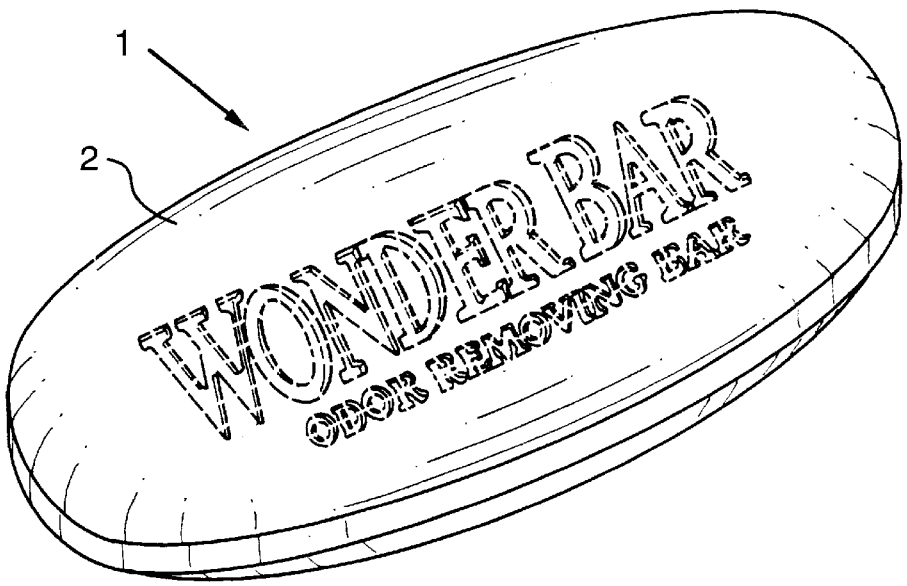
FIG. 1 is a perspective view of the deodorizer bar.
Figure 2:
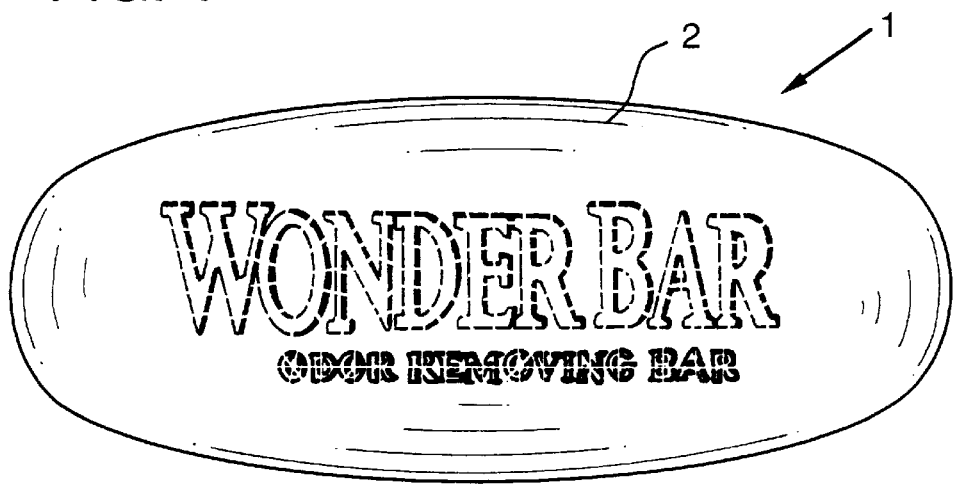
FIG. 2 is a view of the top side of the bar.
Figure 3:
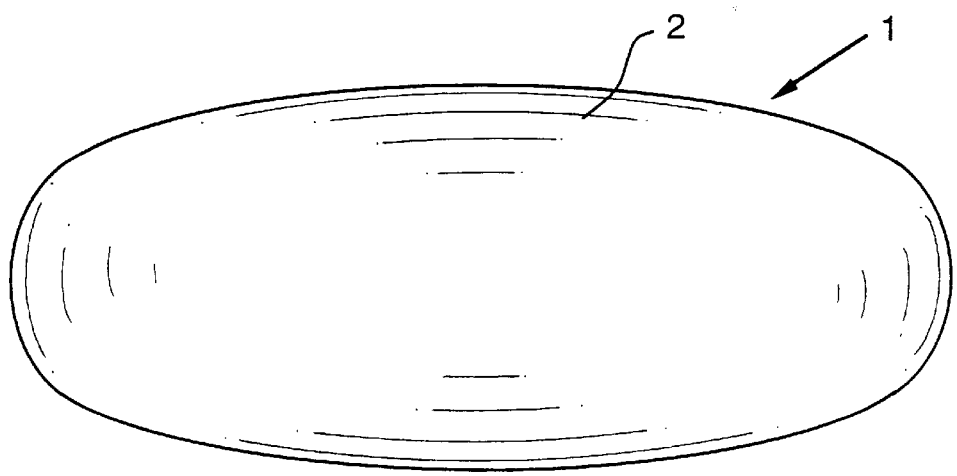
FIG. 3 is a view of the bottom side of the bar.
Figure 4:
FIG. 4. is a view of side aspect of bar.
Figure 5:
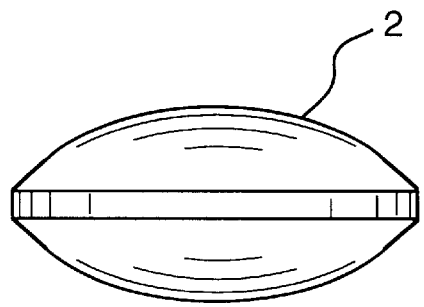
FIG. 5 is a view of end aspect of bar.
Figure 6:
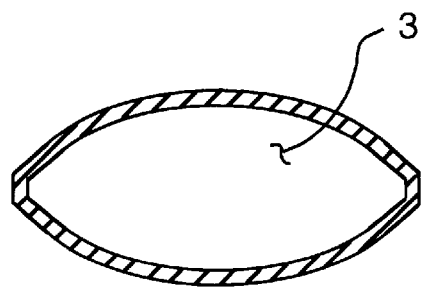
FIG. 6 is a cross-sectional view of the bar.

The deodorizer bar is a permanent, hollow, buoyant, odor removing device (1) which may be viewed in perspective in FIG. 1. The device (1) has a smooth surface in an oval shape. The external surface (2) of the bar best viewed in cross sectional view in FIG. 6 is comprised of metal alloy, with a thickness of 0.6 mm. The internal aspect (3) of device (1) is comprised of air. The external surface (2) bears the name Wonder Bar, a mark applied for by the Inventor with the application Ser. No. 75/225373 and filing date Jan. 14, 1997. The invention works by a process of absorption whereby odor molecules bond to the alloy instead of the hands as one rubs the bar, and are then washed away by liquid. Unlike bars of soap, the invention will not disintegrate.

I claim:

1. I claim a permanent metallic odor removing device, wherein the improvement comprises a smooth external surface made of metal alloy which when rubbed and then immersed in liquid removes odors from hands by process of absorption whereby odor molecules bond to said metal alloy and are washed away by liquid and an internal aspect filled with air, which allows the invention to float in water.

2. I claim in a permanent metallic odor removing device, wherein the improvement comprises a smooth external surface made of metal alloy which when rubbed and then immersed in liquid, removes odors from hands by process of absorption whereby odor molecules bond to said metal alloy and are washed away by liquid and an internal aspect filled with air, which allow the invention to float in water, an external surface which is of a thickness of 0.6 mm.

3. I claim in a permanent metallic odor removing device as in claim 2, wherein the improvement comprises a smooth external surface (2) made of metal alloy which when rubbed and then immersed in liquid, removes odors from hands by process of absorption whereby odor molecules bond to said metal alloy and are washed away by liquid and an internal aspect (3) filled with air, which allow the invention to float in water, an external surface which is an oval shape.

* * * * *